United States Patent [19]
Patrick

[11] Patent Number: 5,593,402
[45] Date of Patent: Jan. 14, 1997

[54] LAPAROSCOPIC DEVICE HAVING A DETACHABLE DISTAL TIP

[75] Inventor: Algird Patrick, Franklin Park, N.J.

[73] Assignee: Biosearch Medical Products Inc., Somerville, N.J.

[21] Appl. No.: 338,417

[22] Filed: Nov. 14, 1994

[51] Int. Cl.$^6$ .......................... A61B 19/00; A61B 17/28
[52] U.S. Cl. ................... 606/1; 606/205; 604/902
[58] Field of Search ....................... 606/1, 110, 113, 606/127, 151, 213, 205–211, 167, 170–180; 128/749–754; 604/902

[56] References Cited

U.S. PATENT DOCUMENTS

| | | |
|---|---|---|
| 2,516,628 | 7/1950 | Held . |
| 2,531,730 | 11/1950 | Henderson . |
| 2,555,493 | 6/1951 | Kirschbaum . |
| 2,790,437 | 4/1957 | Moore . |
| 3,335,727 | 8/1967 | Spoto . |
| 3,506,012 | 4/1970 | Brown . |
| 4,669,611 | 10/1987 | Bowden . |
| 4,997,419 | 3/1991 | Lakatos et al. . |
| 5,052,402 | 10/1991 | Bencini et al. . |
| 5,275,613 | 1/1994 | Haber et al. . |
| 5,290,294 | 3/1994 | Cox et al. ......................... 606/127 |
| 5,304,203 | 4/1994 | El-Mallawany et al. . |
| 5,308,358 | 5/1994 | Bond et al. . |
| 5,320,635 | 6/1994 | Smith ................................ 606/180 |
| 5,336,238 | 8/1994 | Holmes et al. ..................... 606/205 |
| 5,352,235 | 10/1994 | Koros et al. . |
| 5,368,606 | 11/1994 | Marlow et al. .................... 606/170 |
| 5,441,059 | 8/1995 | Dannan ............................... 606/1 |

OTHER PUBLICATIONS

Mectra Labs, Inc., Advertisment for "The Nibbler," undated, one page.
American Hydro–Surgical Instruments, Advertisement for "Trumpet Valve with SmokEvac," undated, one page.
Innovative Surgical, Inc., Advertisement for Laparoscopic Instruments, undated, one page.
Karl Storz Endoscopy Advertisment for Take–apart Instruments, undated, one page.
Mediflex Surgical Products, Advertisement for Laparoscopic Devices & Instruments, undated, one page.
Accurate Surgical & Scientific Instruments Corporation, Advertisement for High Quality Endoscopic Instruments, undated, one page.

*Primary Examiner*—Glenn Dawson
*Attorney, Agent, or Firm*—Hoffmann & Baron

[57] ABSTRACT

A laparoscopic device allowing for the quick attachment and removal of interchangeable, detachable distal tips on its distal end. The device includes concentrically-arranged inner and outer cannulae having distal ends which are dimensioned to simultaneously cooperate with the detachable distal tip whereby the tip may be selectively locked against rotational and axial motion. The tips may include a variety of surgical tools which are preferably disposable, while the remainder of the device is easily disassembled for sterilization and cleaning.

7 Claims, 10 Drawing Sheets

LAPAROSCOPIC DEVICE HAVING A DETACHABLE DISTAL TIP

BACKGROUND OF THE INVENTION

The present invention relates generally to laparoscopic surgical devices, and, more particularly, to laparoscopic surgical devices having detachable distal tips.

In recent years, the popularity of laparoscopic surgical procedures has increased dramatically. Laparoscopy is the treatment and examination of interior organs through use of a laparoscope, an instrument which can be introduced surgically through, for example, the abdominal wall to examine the intra-abdominal organs. Unlike conventional surgical procedures, only a small incision with minimal resulting trauma to the surrounding tissue is required during laparoscopic surgery.

In a typical laparoscopic procedure, a viewing device as well as a variety of surgical instruments may be employed. The latter might include cutting instruments, lasers, grippers, dissectors, suction/irrigation devices, monopolar or bipolar electro-surgical devices, or the like. Frequent changing of instruments is required.

The majority of currently available laparoscopic surgical devices include permanently fixed tips. Such devices require a surgeon to maintain a plurality of tools in the operating room during a procedure. As a result, the tools which are not currently in use must be carefully handled and/or temporarily stored to insure sterility. Moreover, certain instruments, such as cutting tools, can be worn down during use. In these cases, a surgeon must discard the deteriorated laparoscopic device in exchange for a new device.

There are a limited number of currently available laparoscopic surgical devices which include detachable tips. However, these devices suffer from a variety of disadvantages. In the case of screw-on attachments, difficulties arise in sterilizing female threads and with lack of verifiability of locking. Other devices employ intricate mechanisms which are expensive to manufacture and difficult to sterilize. Some require an external tool to lock and unlock the detachable tip. Still others do not have positive means to lock the tip in place or to indicate to the user whether or not the tip is locked securely.

There is, therefore, a need in the prior art for a laparoscopic device which allows for the quick attachment and removal of interchangeable, detachable tips on its distal end, while providing visual confirmation that the tip is securely locked.

SUMMARY OF THE INVENTION

The present invention, which addresses the needs of the prior art, provides a laparoscopic device having a detachable distal tip. The device includes an inner cannula and an outer cannula. The inner cannula has an inner distal end and an inner operative end, and the outer cannula has an outer distal end and an outer operative end. The outer cannula also has an axial bore sufficiently large to permit insertion of the inner cannula. The axial bore of the outer cannula further permits rotational and axial movement between the inner cannula and the outer cannula. The distal ends of the cannulae are dimensioned to simultaneously cooperate with the detachable distal tip upon rotation of the cannulae to selectively lock and unlock the tip.

In a preferred embodiment, the operative ends of the cannulae are dimensioned to provide assembly and cooperative movement therebetween. Preferably, the lengths of the cannulae are substantially coextensive with one another, to facilitate cooperative action therebetween. The inner cannula includes one or more slots, preferably two equally spaced, while the tip includes one or more flutes, preferably two equally spaced, which engage the slots of the inner cannula to provide rotational fixity therebetween. The tip also includes axial locking means, preferably a groove defined by a shoulder included on the tip and the ends of the flutes. The outer cannula includes lugs which, in an unlocked position, permit insertion and removal of the tip, and in a locked position, engage the axial locking means to prevent axial translation between the tip and the cannulae. Transition between the locked and the unlocked position is achieved by relative rotation of the cannulae. The operative ends of the cannulae cooperate through a locking and indexing mechanism having first and second handles. One handle is provided with a locking member and the other is provided with a locking member engagement recess. The locking member and engagement recess lock the cannulae against translation, but permit an indexed rotation between the cannulae between a first position where the detachable tip is locked at the distal ends and a second position where the detachable tip is unlocked at the distal ends.

The invention may be adapted to employ an articulation shaft for the actuation of articulated operating tools on the distal tip. The invention may be further adapted to incorporate electrical contacts at the distal end suitable for monopolar or bipolar electrosurgical tips.

As a result, the present invention provides a laparoscopic device which allows for the quick attachment and removal of interchangeable, detachable distal tips on its distal end. The present invention also provides a laparoscopic device which allows for visual confirmation that the detachable tip is locked in position. The present invention further provides a laparoscopic device which allows for rapid disassembly for total sterilization. The cannulae are separable and the detachable distal tips may advantageously be made disposable.

DETAILED DESCRIPTION OF THE INVENTION

Figure 1:
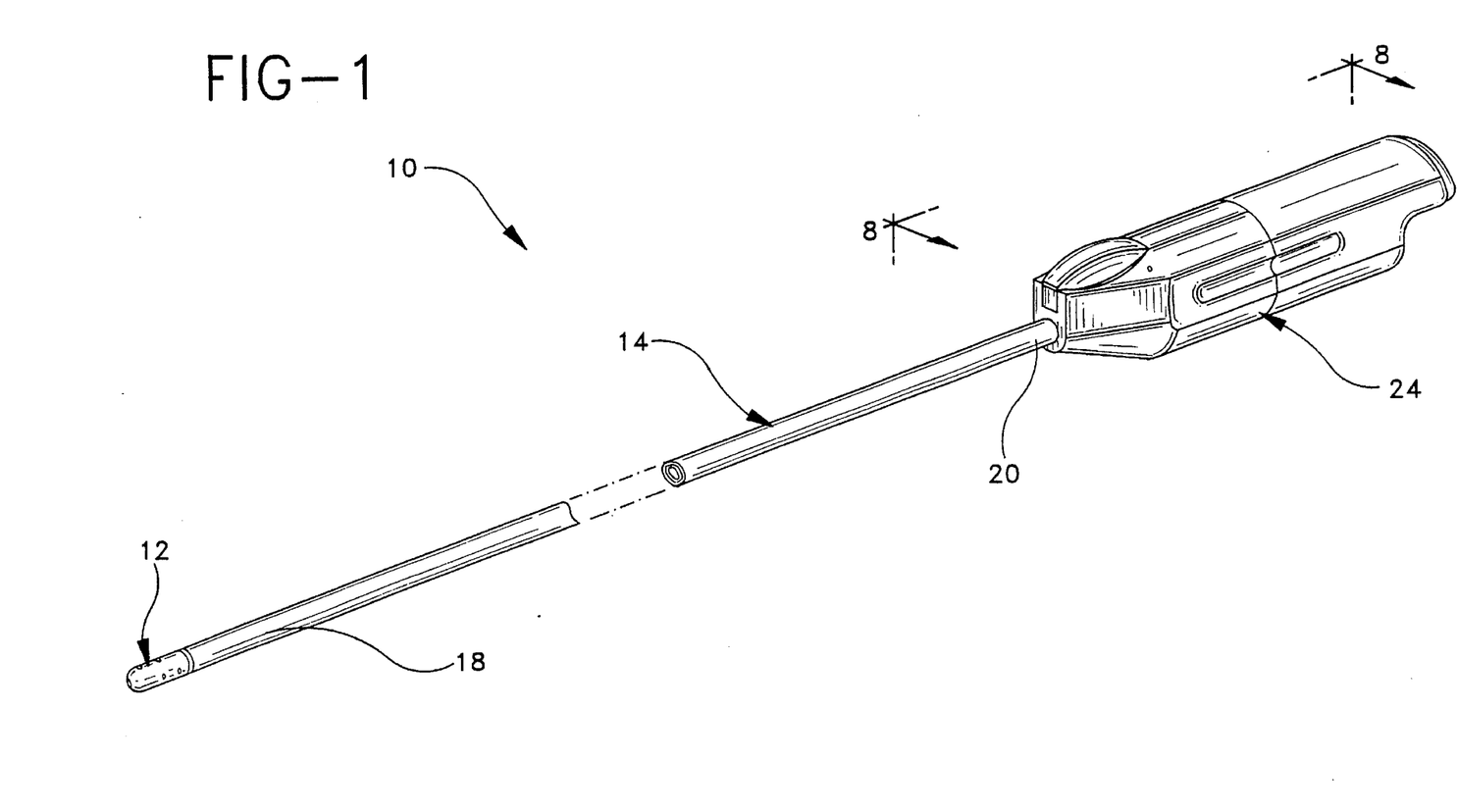
FIG. 1 is a perspective view of a laparoscopic device in accordance with the present invention.
Figure 2:
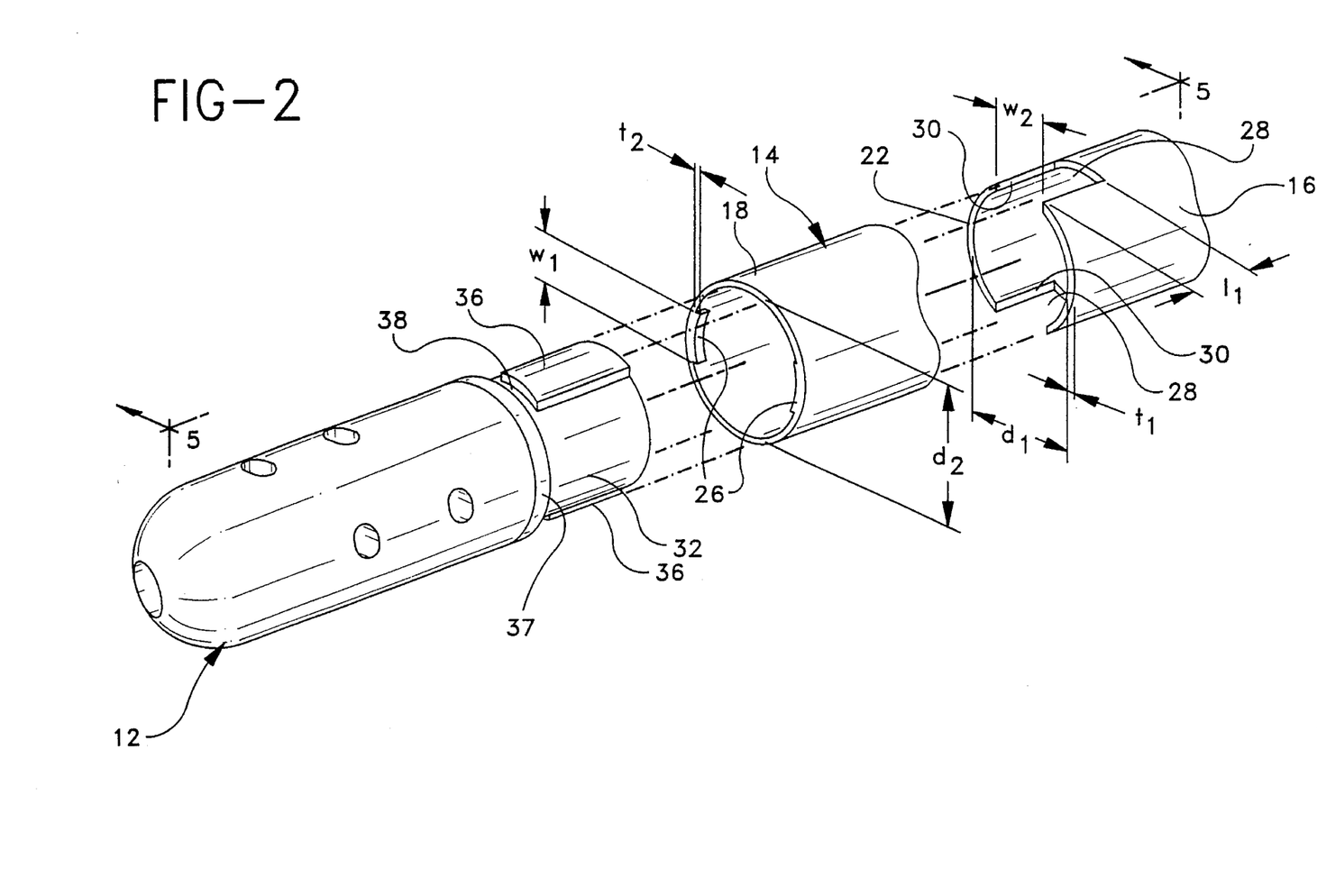
FIG. 2 is an enlarged, exploded perspective view of the distal end of the laparoscopic device of FIG. 1.
Figure 7:
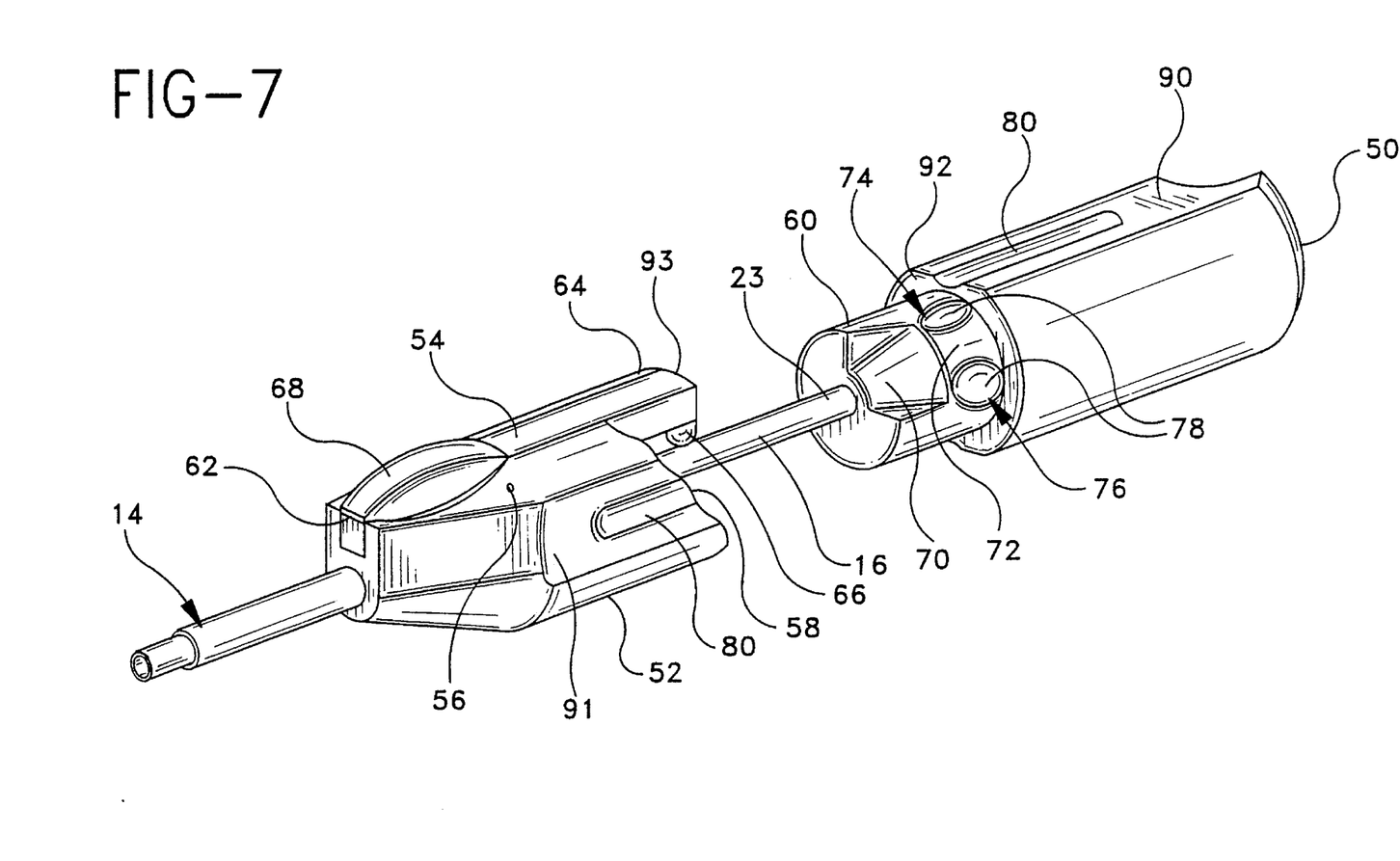
FIG. 7 is an enlarged, exploded, partial cut away perspective view of the operative end of the laparoscopic device of FIG. 1.

Referring to the drawings, FIG. 1 shows an assembled laparoscopic device 10. The assembly includes a detachable distal tip 12, an outer cannula 14, and an inner cannula 16 (as best shown in FIG. 2). The outer cannula has an outer distal end 18, and an outer operative end 20. The inner cannula has an inner distal end 22 (as shown in FIG. 2) and an inner operative end 23 (as shown in FIG. 7). The inner and outer cannulae are capable of relative axial and rotational movement. The inner cannula and outer cannula can be locked against relative movement by any appropriate means. Such means can include an indexing mechanism 24 positioned at the operative end. The cannulae are preferably made of surgical stainless steel, although materials such as titanium and plastic are also contemplated.

FIG. 2 shows the outer distal end 18 of the outer cannula 14 and the inner distal end 22 of the inner cannula 16. The outer cannula has an inside diameter suitably sized to permit insertion of the inner cannula into the outer cannula and to further permit free rotation between the inner and outer cannulae. The inner cannula is preferably hollow to allow internal access to the tool positioned at the distal end. Of course, embodiments of the invention wherein the inner cannula comprises instead a solid member are also contemplated. The inner distal end preferably has a wall thickness $t_1$ and an inside diameter $d_1$.

Tip 12 is releasably attached to the distal end of device 10 and may be selectively locked against axial and rotational movement. Particularly, the distal ends of the cannulae are configured and dimensioned to simultaneously cooperate with the tip, thereby securing the tip and locking it against movement, upon rotation of the cannulae.

In one preferred embodiment, the outer distal end 18 includes one or more locking lugs 26 which secure the tip against axial movement when device 10 is in the locked position. Preferably two lugs are provided, which are spaced about 180 degrees apart and have a width $w_1$ equal to about ½ of the inside diameter $d_2$ of the outer cannula. The locking lugs project inward towards the center of the outer cannula a distance $t_2$ preferably equal to the wall thickness $t_1$ of the inner cannula and are dimensioned to releasably engage the detachable distal tip.

In this preferred embodiment, the inner distal end includes one or more slots 28, preferably two, sized to receive rotational locking members, e.g., flutes 36, positioned on the detachable distal tip. The slots include slot walls 30 and are spaced about 180 degrees apart in the preferred embodiment. The slots have a width $w_2$ equal to about ½ of the inside diameter of the outer cannula, and a suitable predetermined length $l_1$.

Figure 6:
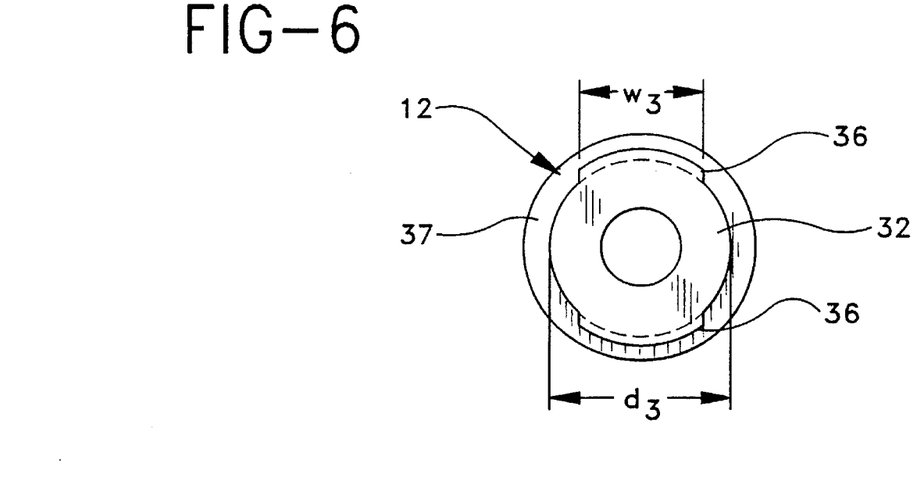
FIG. 6 is an end view of the detachable distal tip of FIG. 5.

The detachable tip 12 includes an insertion end 32. The insertion end has an outside diameter $d_3$ (as shown in FIG. 6) substantially equal to the inside diameter of the inner cannula, to permit the insertion end to be inserted freely into the inner cannula and securely supported thereby. The insertion end has a length approximately equal to the length of the slots in the inner distal end. As mentioned, the insertion end is provided with one or more flutes 36.

Preferably, two flutes are provided. The flutes extend outwardly from the insertion end so as to be substantially equal to the inside diameter of the outer cannula.

The width $w_3$ of the flutes (as shown in FIG. 6) is substantially equal to that of the slots in the inner distal end and the length of the flutes is selected for full insertion into the slots. The detachable distal tip further includes shoulder 37 which is dimensioned to abut distal end 18 of the outer cannula when the tip is fully inserted therein. The length of the flutes 36 is less than the length of the insertion end 32, thereby providing a lug receiving groove 38 between the flutes and shoulder 37.

Of course, other arrangements whereby the distal ends of the cannulae cooperate to selectively lock the detachable tip against rotational and axial movement are also contemplated.

Referring to FIG. 2, when the inner cannula and outer cannula are in a first, unlocked position, the detachable distal tip can be inserted into the inside diameter of the inner distal end by aligning the flutes 36 with the slots 28 of the inner distal end.

Figure 3:
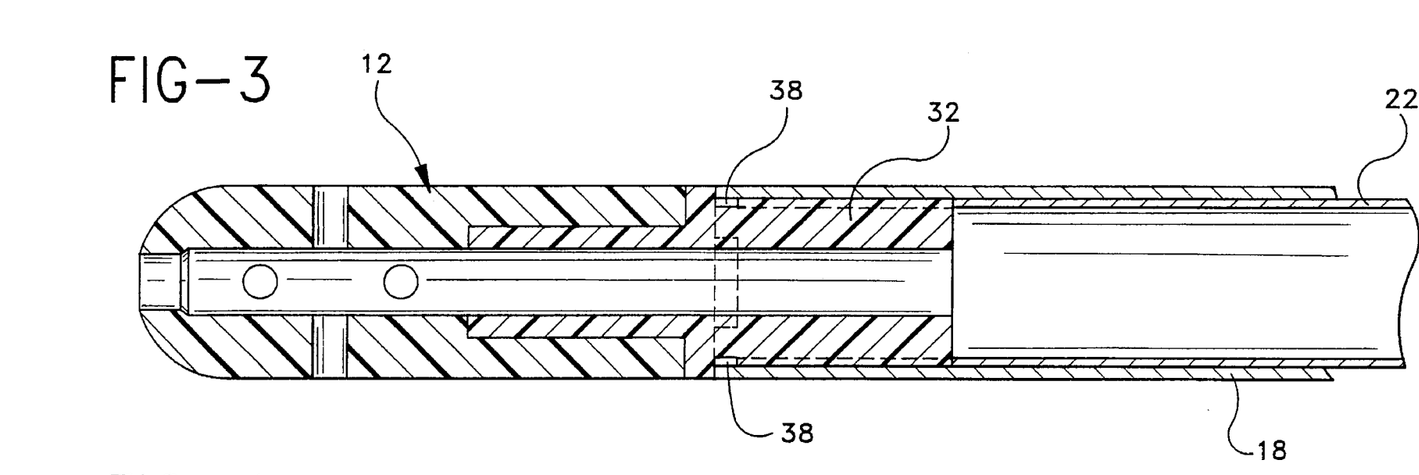
FIG. 3 is a sectional view of the distal end in an unlocked condition.
Figure 3A:
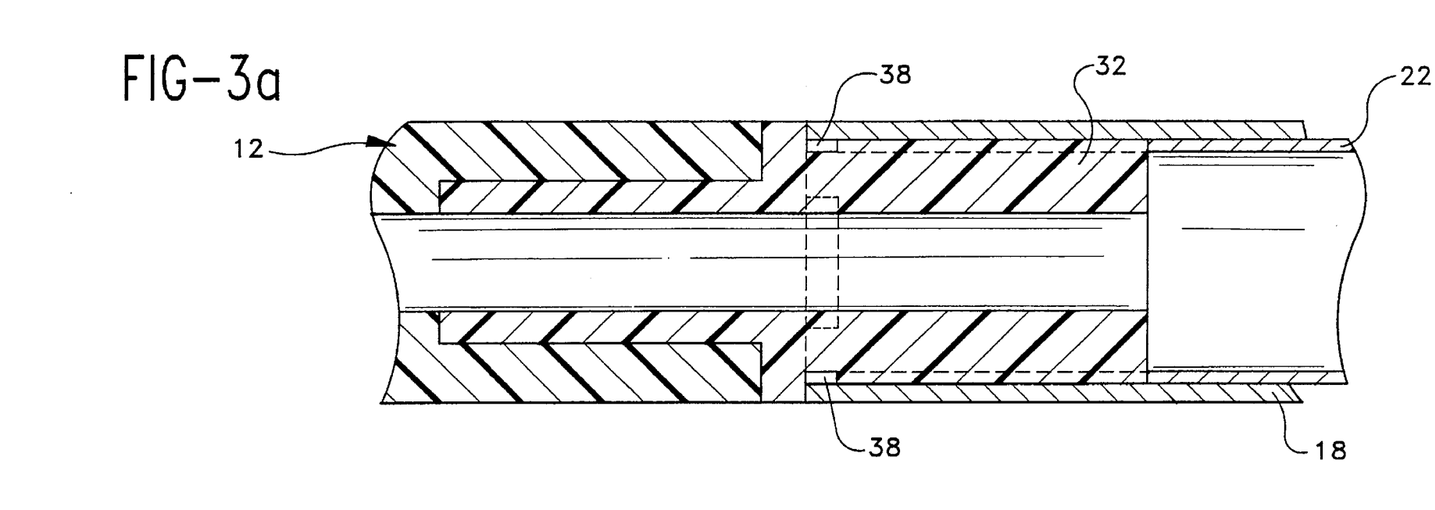
FIG. 3a is an enlarged detail of FIG. 3.

FIGS. 3 and 3a show the insertion end 32 of the detachable distal tip 12 engaged with the inner distal end 22, but in an unlocked condition. Lug receiving groove 38 is also shown. By rotating the outer distal end and the inner distal end with respect to each other, the detachable distal tip is locked in place. In the preferred embodiment, the amount of rotation is 90°, corresponding to two each of lugs 26, slots 28, and flutes 36. Other amounts of rotation are possible, depending, for example, on the number of lugs, slots, and flutes. For three each of these items, about 60° of rotation is employed; for four each, about 45°.

Figure 4:
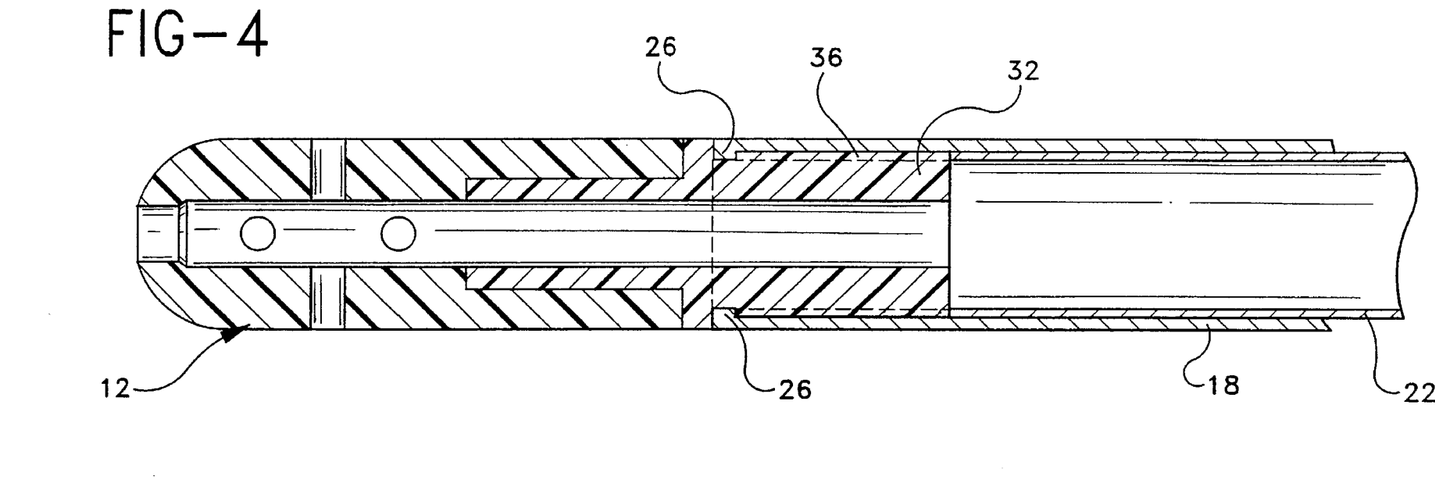
FIG. 4 is a sectional view of the distal end in a locked condition.
Figure 4A:
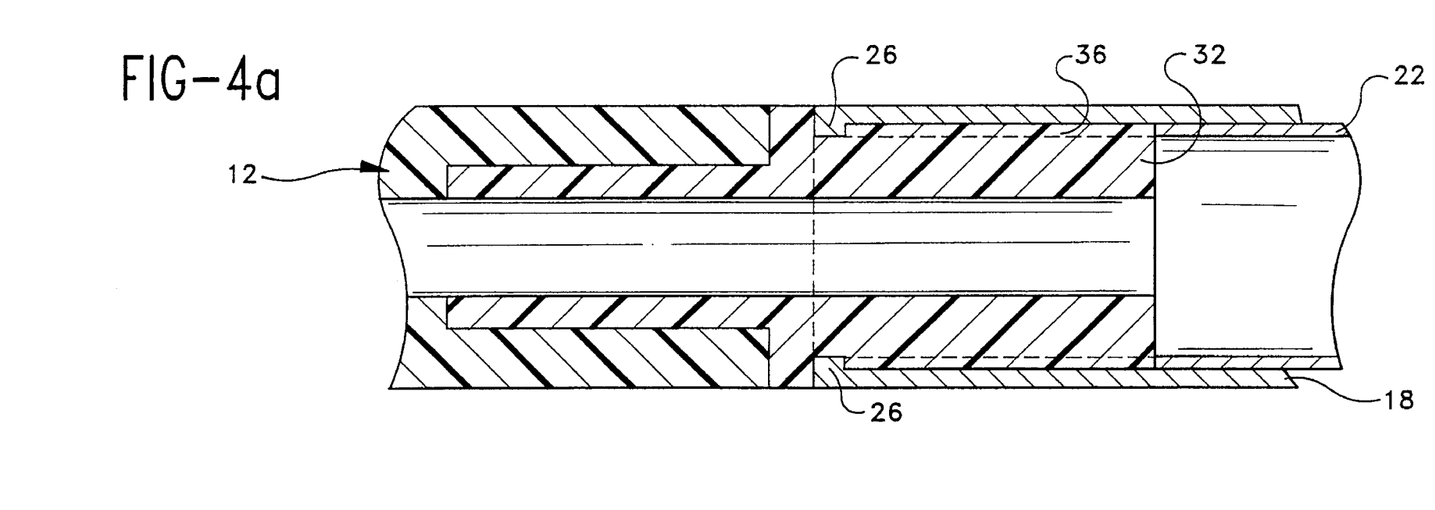
FIG. 4a is an enlarged detail of FIG. 4.

FIGS. 4 and 4a show the detachable distal tip 12 in a locked condition. The 90° relative rotation causes the locking lugs 26 to move through the lug receiving groove 38 (in FIG. 3) and engage the flutes 36. The engagement between the locking lugs and the flutes provides axial fixity between the detachable distal tip and the inner and outer distal ends. The engagement of the flutes 36 against the walls 30 of the slots 28 in the inner distal end, as shown in FIG. 2, provides rotational fixity between the detachable distal tip and the inner and outer distal ends.

Figure 5:
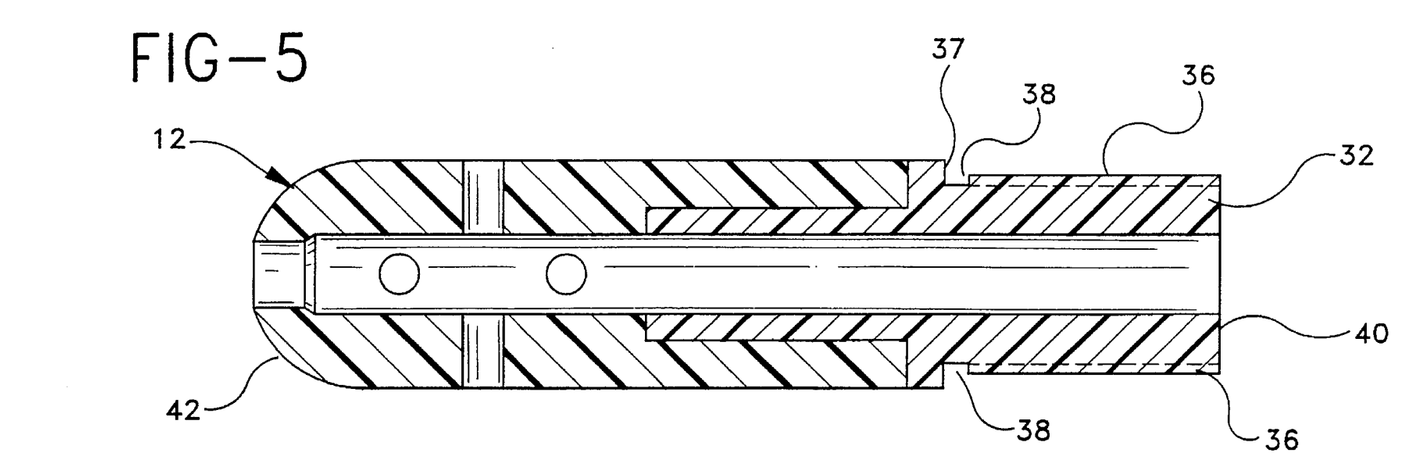
FIG. 5 is a sectional view of the detachable distal tip taken along line 5—5 of FIG. 2.

As shown in FIG. 5, lug receiving groove 38 is formed between the ends of the flutes 36 and shoulder 37. The locking lugs, as shown in FIG. 2, can rotate freely within this groove.

Figure 10:
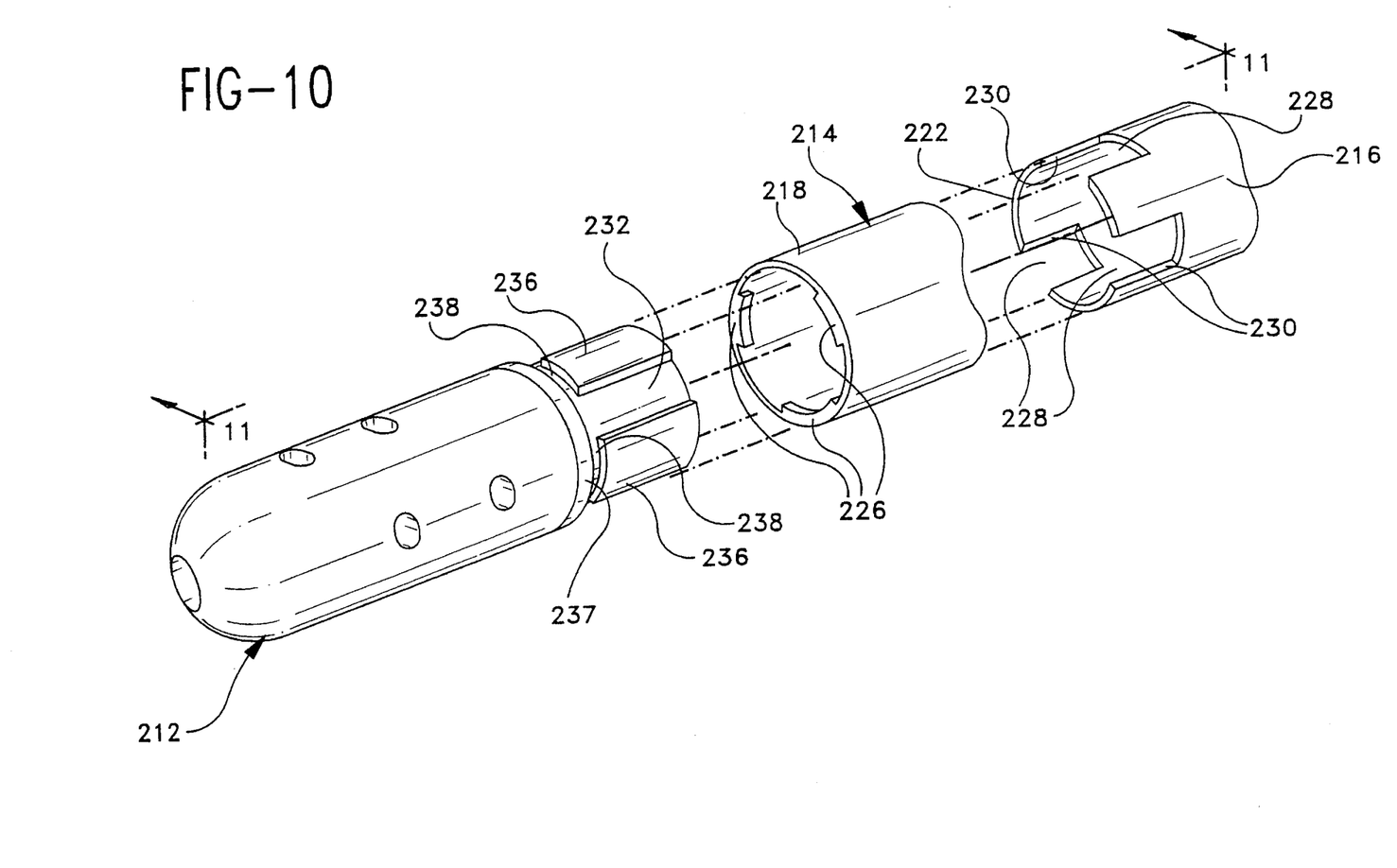
FIG. 10 is a view similar to FIG. 2 showing another alternative embodiment of the present invention.
Figure 11:
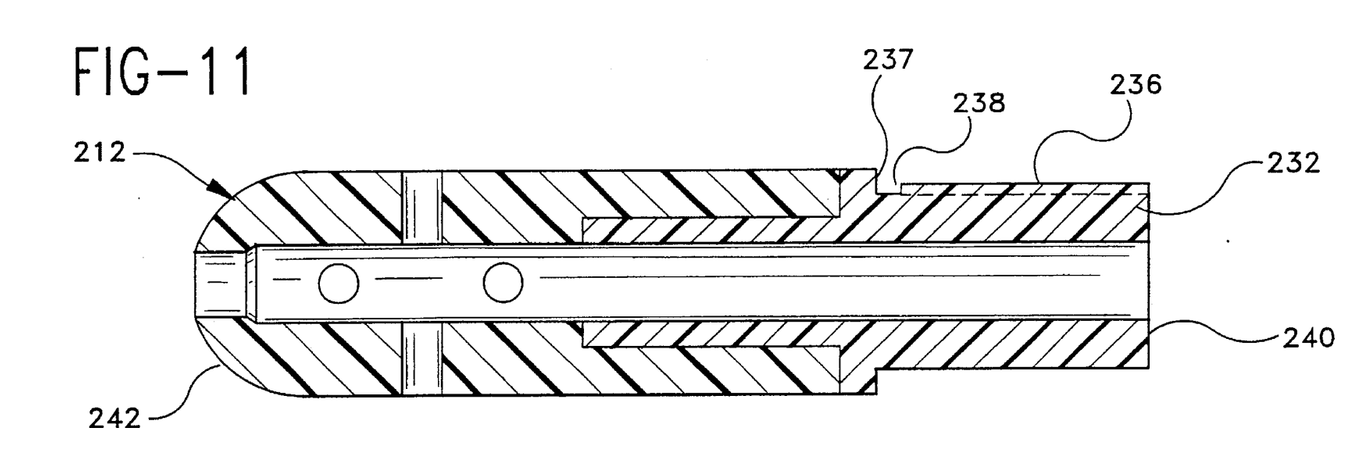
FIG. 11 is a sectional view of the detachable distal tip of the alternative embodiment of FIG. 10 taken along line 11—11 of FIG. 10.
Figure 12:
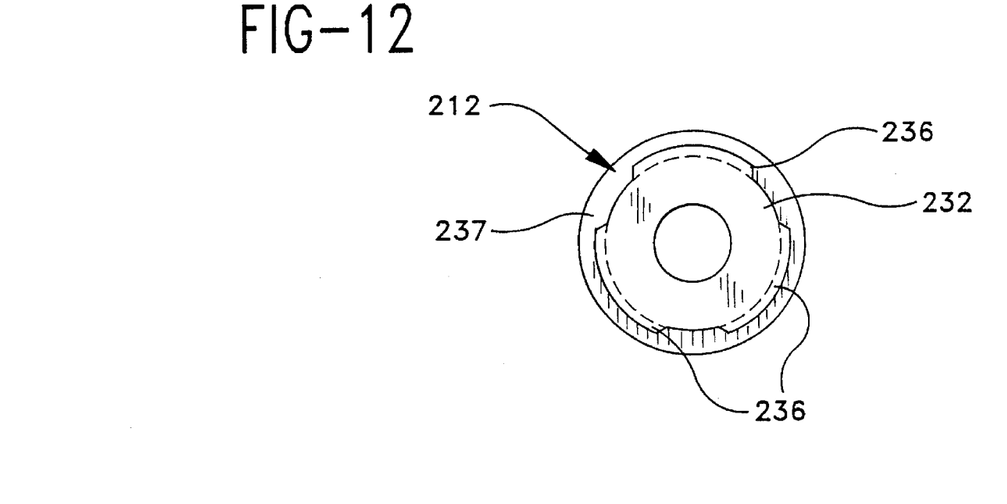
FIG. 12 is an end view of the detachable distal tip of FIG. 11.

The detachable distal tip can be formed integral with an operating tool, or for example, can be an assembly comprising an adapter 40 and an operating tool 42, as shown in FIG. 5. The operating tool can be, for example, a suction cannula, an irrigation cannula, a blunt dissector, a suction Kittner, an irrigation Kittner, an electrosurgical device, a retractor, a sponge stick, or a knot pusher. Articulated operating tools such as grabbers, scissors, and forceps can also be employed by adding an articulation shaft to the device, as discussed below. Monopolar or bipolar electrosurgical tips can be accommodated by providing contacts in the distal ends of the cannulae. Because rotational orientation of the tip relative to the cannulae is controllable in the present invention, bipolar devices can be employed. Preferred materials for the tips will vary depending on their use. For example, suction devices may be advantageously made of plastic, while articulated operating tools may be advantageously made of stainless steel. As shown in FIGS. 10–12, wherein like components have received the same reference numbers as for the first embodiment, incremented by 100, in an alternative embodiment of the present invention, three slots 228 may be formed in inner distal end 222, three locking lugs 226 may be formed in outer distal end 218, and three flutes 236 may be formed on detachable distal tip 212 of device 210. As noted above, about 60° of rotation between the cannulae 214, 216 is employed to lock the tip 212 of this embodiment in place.

Figure 8:
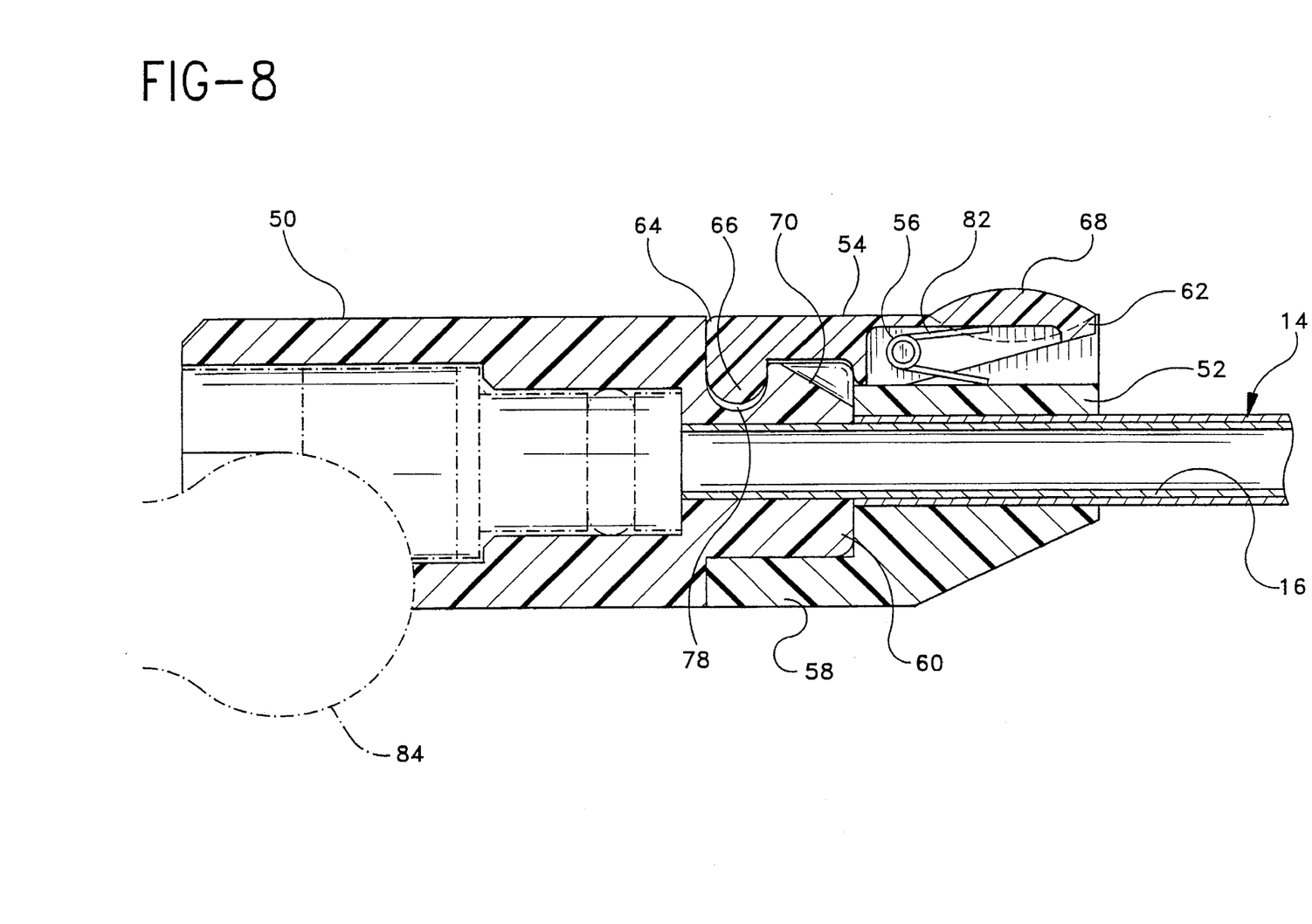
FIG. 8 is sectional view taken along line 8—8 of FIG. 1.

The locking and indexing mechanism 24 is shown in detail in FIG. 7. The mechanism includes a first handle 50 which is fastened to the inner cannula 16. A second handle 52 is fastened to the outer cannula 14. Handles 50, 52 may be made of a plastic such as acetal, ABS, or liquid crystal polymer, or of a metal such as titanium or stainless steel. The inner cannula is inserted within the outer cannula. A locking member such as locking lever 54 is mounted to one of the handles, preferably to the second handle 52, and pivots about pin 56. The first handle preferably includes a protruding neck 60 and the second handle preferably includes an end 58 provided with a bore which is dimensioned to receive protruding neck 60. Locking lever 54 has an actuating end 62 and a locking end 64. A locking ball 66 projects inwards from the locking end of the locking lever. A resilient member 82, as shown in FIG. 8, biases the ball towards the bore of end 58. A button 68 for finger actuation is provided at the actuating end of the locking lever.

Protruding neck 60 has a locking member engagement recess, preferably comprising both a tapered portion 70, and an immediately adjacent circumferential groove 72. As the first handle 50 is inserted into the second handle 52, the ball 66 is engaged by the tapered portion and is cammed up the tapered portion 70 and snapped into groove 72 thereby locking the first and second handles against axial translation. The groove 72 has a first end 74 and second end 76 each provided with a ball detent 78. While the ball engaged in the groove 72 prevents axial translation, rotation between the cannulae is possible over a range equal to the angle subtended by the circumferential groove 72. At either end of the rotation, the ball engages the ball detents 78 providing an index between an unlocked position and a locked position. At a first, unlocked position, corresponding to ball 66 in detent 78 at end 74, the cannulae can be oriented to accept a distal tip. At a second, locked position, corresponding to ball 66 in detent 78 at end 76, the distal tip can be locked in place. Visual alignment marks 80 on the first and second handles verify tip locking.

The handles 50, 52 are preferably configured with surface relief which indicates when the tip is locked, as well. For example, surfaces 90 and 91 found on handles 50 and 52, respectively, create irregular cross-sections 92 and 93, respectively, which are congruent when the device is in the locked position.

As shown in FIG. 8, first handle 50 is fastened to inner cannula 16, while second handle 52 is fastened to outer cannula 14. As described above, locking lever 54 has locking ball 66, locking end 64, button 68, and actuating end 62. Resilient member 82 can be, for example, a torsional coil spring which biases the locking lever 54. Ball 66 is biased into ball detent 78, thereby locking handles 50, 52 against translation and indexing the handles for relative rotation. Locking lever 54 pivots on pin 56. End 58 with bore of second handle 52 accepts protruding neck 60 of first handle 50. Locking ball 66 is cammed over tapered portion 70 during assembly. First handle 50 can be dimensioned to interface with, for example, a suction/irrigation valve 84.

Figure 9:
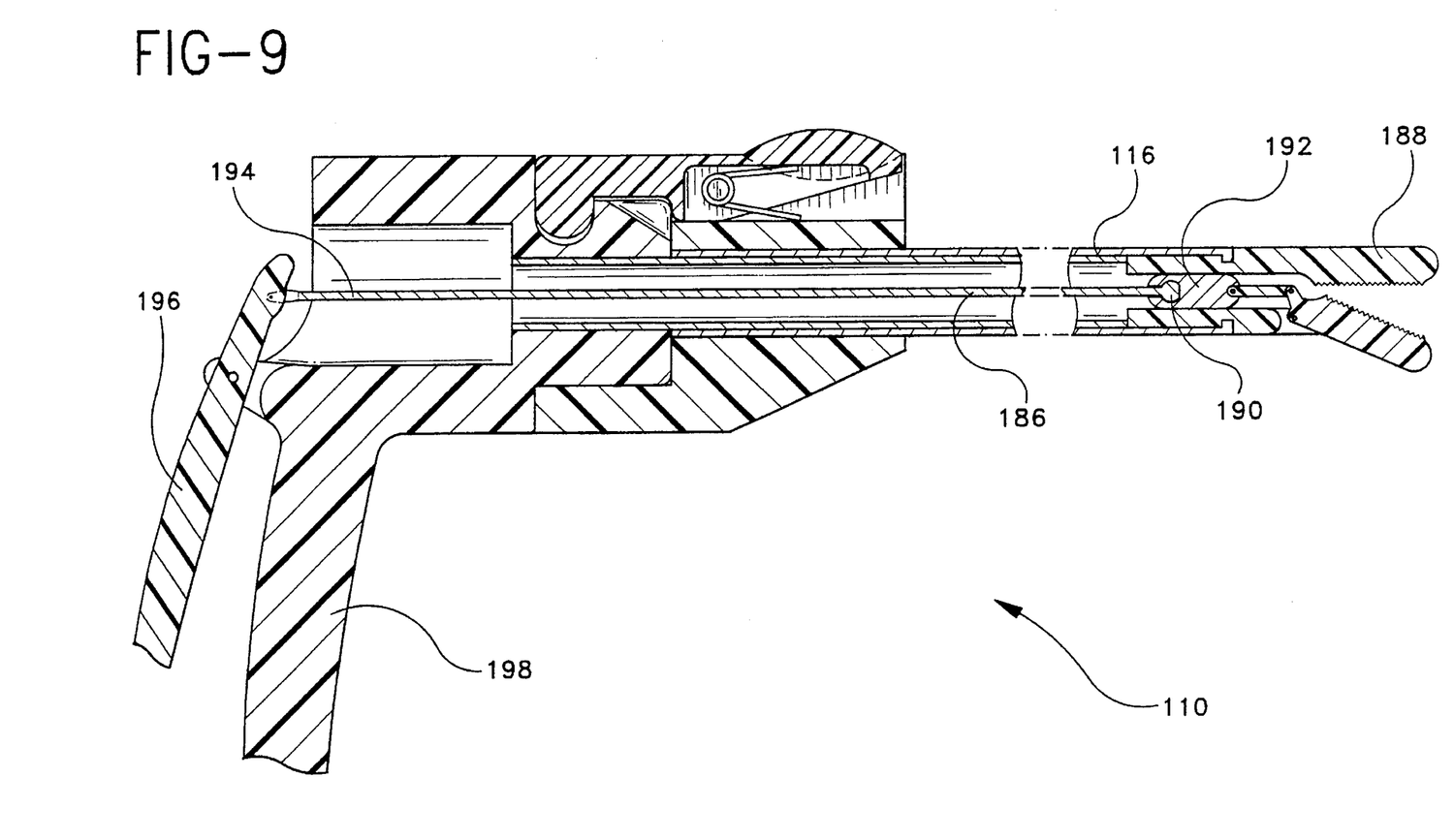
FIG. 9 is a sectional view of an alternative embodiment of the present invention which incorporates an articulation shaft.

FIG. 9 shows an alternative embodiment of the present invention, i.e., laparoscopic device 110 which includes an articulation shaft 186 to actuate an articulated operating tool 188. The articulation shaft is preferably reusable and may be mounted within inner cannula 116, preferably by suitable linear bearing means (not shown). The shaft has a distal end 190 that engages articulated operating tool interface member 192 upon insertion of the tool into the distal ends of the cannulae. Any suitable means of semi-permanent engagement, such as a ball lock, may be employed. The articulation shaft 186 has a proximal end 194 that is pivotally attached to a movable grip 196. When movable grip 196 is squeezed towards fixed grip 198, shaft 186 retracts interface member 192 to articulate tool 188.

While there have been described what are presently believed to be the preferred embodiments of the invention, those skilled in the art will realize that various changes and modifications may be made to the invention without departing from the spirit of the invention, and it is intended to claim all such changes and modifications as fall within the scope of the invention.

What is claimed:

1. A laparoscopic device comprising:

an inner cannula having an inner distal end and an inner operative end;

a detachable distal tip having a tip locking device thereon;

an outer cannula having an outer distal end and an outer operative end, said outer cannula dimensioned for insertion of said inner cannula therein and for free rotation therebetween, said inner cannula positioned inside said outer cannula, said distal ends including first and second end locking apparatus on said inner and outer distal ends respectively, said first and second end locking apparatus configured and dimensioned to simultaneously cooperate with said tip locking device of said detachable distal tip upon rotation between said inner distal end and said outer distal end, whereby said detachable distal tip may be selectively locked, relative to said distal ends, against rotational and axial movement; and a mechanism operatively associated with said inner and outer cannulae for providing selective axial locking between said cannulae;

wherein:

said tip locking device of said detachable distal tip includes an insertion end of said tip having a rotational locking member and axial locking means thereon;

said first end locking apparatus includes a slot dimensioned to receive said rotational locking member thereby providing rotational fixity between said detachable distal tip and said distal ends; and said second end locking apparatus includes a locking lug dimensioned to engage said axial locking means thereby providing translational fixity between said detachable distal tip and said distal ends.

2. The device in accordance with claim 1, wherein:

said inner cannula is provided with a bore and has an inside diameter, an outside diameter, and a wall thickness;

said outer cannula is provided with a bore and has an inside diameter and an outside diameter;

said detachable distal tip includes a shoulder adjacent said insertion end;

said insertion end has a length and an outside surface with a diameter equal to said inner cannula inside diameter;

said rotational locking member is located on said outside surface of said insertion end and is spaced from said shoulder a predetermined amount defining a lug receiving groove sized to receive said lug.

3. The device in accordance with claim 2, wherein:

said mechanism operatively associated with said inner and outer cannulae provides selective rotational locking between said cannulae;

said first end locking apparatus includes a pair of said slots spaced 180 degrees apart;

said second end locking apparatus includes a pair of said lugs spaced 180 degrees apart;

said detachable distal tip includes a pair of said rotational locking members spaced 180 degrees apart; and said cannulae lock in a locked position corresponding to a predetermined relative rotation between said cannulae.

4. The device in accordance with claim 2, wherein:

said mechanism operatively associated with said inner and outer cannulae provides selective rotational locking between said cannulae;

said first end locking apparatus includes three of said slots spaced 120 degrees apart;

said second end locking apparatus includes three of said lugs spaced 120 degrees apart;

said detachable distal tip includes three of said rotational locking members spaced 120 degrees apart; and said cannulae lock in a locked position corresponding to a predetermined relative rotation between said cannulae.

5. The device in accordance with claim 1, wherein said detachable distal tip is a laparoscopic operating tool.

6. The device in accordance with claim 5, wherein said tool is non-articulated.

7. The device in accordance with claim 5, wherein said tool is articulated relative to said outer distal end.

* * * * *